(12) United States Patent
Ducki et al.

(10) Patent No.: US 10,214,476 B2
(45) Date of Patent: Feb. 26, 2019

(54) PAIN RELIEF COMPOUNDS

(71) Applicants: ECOLE NATIONALE SUPERIEURE DE CHIMIE DE CLERMONT FERRAND, Aubiere (FR); Université Clermont Auvergne, Clermont Ferrand (FR)

(72) Inventors: Sylvie Ducki, Aubiere (FR); Khalil Bennis, Clermont Ferrand (FR); Alain Eschalier, Chamalieres (FR); Jérôme Busserolles, Saulzet (FR); Florian Lesage, Valbonne (FR); Nuno Rodrigues, Aubiere (FR); Delphine Vivier, Lempdes (FR)

(73) Assignees: ECOLE NATIONALE SUPERIEURE DE CHIMIE DE CLERMONT FERRAND, Aubiere (FR); UNIVERSITÉ CLERMONT AUVERGNE, Clermont Ferrand (FR)

( * ) Notice: Subject to any disclaimer, the term of this patent is extended or adjusted under 35 U.S.C. 154(b) by 41 days.

(21) Appl. No.: 14/369,674

(22) PCT Filed: Dec. 31, 2012

(86) PCT No.: PCT/EP2012/077113
§ 371 (c)(1),
(2) Date: Jun. 27, 2014

(87) PCT Pub. No.: WO2013/098416
PCT Pub. Date: Jul. 4, 2013

(65) Prior Publication Data
US 2015/0038466 A1 Feb. 5, 2015
US 2015/0274633 A2 Oct. 1, 2015

(30) Foreign Application Priority Data

Dec. 30, 2011 (FR) ..................... 11 62564

(51) Int. Cl.
| | | |
|---|---|---|
| *C07C 57/60* | (2006.01) | |
| *C07D 209/18* | (2006.01) | |
| *C07D 209/42* | (2006.01) | |
| *C07D 307/54* | (2006.01) | |
| *C07C 229/34* | (2006.01) | |
| *C07C 255/41* | (2006.01) | |
| *C07F 9/12* | (2006.01) | |
| *C07F 9/09* | (2006.01) | |

(52) U.S. Cl.
CPC ............ *C07C 57/60* (2013.01); *C07C 229/34* (2013.01); *C07C 255/41* (2013.01); *C07D 209/18* (2013.01); *C07D 209/42* (2013.01); *C07D 307/54* (2013.01); *C07F 9/09* (2013.01); *C07F 9/12* (2013.01); *C07C 2601/14* (2017.05)

(58) Field of Classification Search
None
See application file for complete search history.

(56) References Cited

U.S. PATENT DOCUMENTS

| | | | | |
|---|---|---|---|---|
| 4,297,519 A | * | 10/1981 | Ertel | ..................... C07C 201/12 204/157.82 |
| 4,885,006 A | | 12/1989 | Grollier et al. | |
| 5,063,243 A | * | 11/1991 | Cho | ..................... C07C 255/34 514/438 |
| 5,652,250 A | * | 7/1997 | Buzzetti | ................ C07C 255/41 514/352 |
| 2007/0259051 A1 | | 11/2007 | Feinmark et al. | |
| 2010/0275986 A1 | | 11/2010 | Lin et al. | |
| 2012/0260354 A1 | | 10/2012 | Eschalier | |

FOREIGN PATENT DOCUMENTS

| | | |
|---|---|---|
| CA | 2 012 634 A1 | 9/1991 |
| CN | 101407639 A | 4/2009 |
| CN | 102181171 A | 9/2011 |
| CN | 102250484 A | 11/2011 |
| CN | 102276600 A | 12/2011 |
| DE | 164 296 C | 12/1902 |
| EP | 0572 167 A1 | 12/1993 |
| EP | 1 932 833 A1 | 6/2008 |
| JP | 2011-246503 A | 12/2011 |
| WO | WO 2004/016616 A1 | 2/2004 |
| WO | WO 2010/062900 A2 | 6/2010 |
| WO | WO 2010/062900 A3 | 6/2010 |
| WO | WO 2011/033241 A1 | 3/2011 |

OTHER PUBLICATIONS

Lewis, R Hawley's Condensed Chemical Dictionary, 15th ed., 2007, p. 711.*
Freeman, F. et al. J. Amer. Chem Soc. 1986, vol. 108, 4504-09.*
CAPLUS 1989 192679.*
Zhao, G-L Tet. Lett. 2009 vol. 50 pp. 3458-3462.*
Hawleys Condensed Chemical Dictionary ,2011, excerpt.*
CAPLUS 1978:105043.*
Danthi et al, "Caffeic Acid Esters Activate TREK-1 Potassium Channels and Inhibit Depolarization-Dependent Secretion", Molecular Pharmacology, vol. 65, No. 3, 2004, pp. 599-610.
Guyot J. et al: Cinétique et mécanisme de la Réaction de knoevenagel dans le Benzène-2, Tetrahedron, Elsevier Science Publishers, Amsterdam, NL, vol. 39, No. 7, Jan. 1, 1983, pp. 1167-1179.
Simpson J et al: "New solid phase Knoevenagel catalyst", Tetrahedron Letters, Elsevier, Amsterdam, NL, vol. 40, No. 38, Sep. 17, 1999, pp. 7031-7033.
Van Order et al, "3-Indole aldehyde and certain of its condensation products", Journal of Organic Chemistry, American Chemical Society, Easton.; US, vol. 10, No. 2, Mar. 1, 1945, pp. 128-133.
Zhao et al, "Organocatalytic enantioselective domino synthesis of highly functionalized cyclohexanes with an all-carbon quaternary stereocenter", Tetrahedron Letters, Elsevier, Amsterdam, NL, vol. 50, No. 26, Jul. 1, 2009, pp. 3458-3462.

(Continued)

*Primary Examiner* — Heidi Reese
(74) *Attorney, Agent, or Firm* — Knobbe, Martens, Olson & Bear, LLP

(57) ABSTRACT

The present invention relates to the use of compounds for the treatment or prevention of pain in mammals, in particularly in human beings, and also to a process for preparing these compounds.

8 Claims, No Drawings

(56) References Cited

OTHER PUBLICATIONS

French Preliminary Search Report, regarding FR 1162564, dated Aug. 21, 2012, in 5 pages.
International Search Report, re International Application No. PCT/EP2012/077113, dated Apr. 7, 2013, in 7 pages.
Elbannany et al., Synthesis of Pyrrole, Pyrrolidone, Pyrrolo[3,4-c]Pyrazole, Pyrrolo[3,2-b]Pyridine and Pyrrolo[3,2-b]Pyrrole Derivatives, Heterocycles, vol. 27, No. 9, pp. 2071-2075, 1988.
Danthi, S., et al., Caffeic Acid Esters Activate TREK-1 Potassium Channels and Inhibit Depolarization-Dependent Secretion, Molecular Pharmacology, vol. 65, pp. 599-610, 2004.
Freeman, F., et al., Permanganate Ion Oxidations. 17. Kinetics and Mechanism of the Oxidation of (E)-3-(2-Thienyl)-2-propenoates and (E)-3-(3-Thienyl)-2-propenoates in Phosphate-Buffered Solutions, J. Am. Chem. Soc., vol. 108, pp. 4504-4509, 1986.
Sharma, Y.O., et al., $CO_2$ absorbing cost-effective ionic liquid for synthesis of commercially important alpha cyanoacrylic acids: A safe process for activation of cyanoacetic acid, Green Chem., vol. 11, pp. 526-530, 2009.
Van Order, R.B., et al., 3-Indole aldehyde and certain of its condensation products, J. Org. Chem., vol. 10, No. 2, pp. 128-133, 1945.
Vivier, D., et al, Perspectives on the Two-Pore Domain Potassium Channel TREK-1 (TWIK-Related $K^+$ Channel 1). A Novel Therapeutic Target?, J. Med. Chem., vol. 59, pp. 5149-5157, 2016.
Vivier, D., et al., Development of the First Two-Pore Domain Potassium Channel TWIK-Related $K^+$ Channel 1-Selective Agonist Possessing in Vivo Antinociceptive Activity, J. Med. Chem., vol. 60, No. 3, pp. 1076-1088, 2017.
Zhao, G-L, et al., Organocatalytic enantioselective domino synthesis of highly functionalized cyclohexanes with an all-carbon quaternary stereocenter, Tetrahedron Letters, vol. 50, pp. 3458-3462, 2009.
Garcia-Rubia, A., et al. Palladium (II)-Catalyzed Regioselective Direct C2 Alkenylation of Indoles and Pyrroles Assisted by the N-(2-Pyridyl)sulfonyl Protecting Group, Angew Chem. Int., vol. 48, pp. 6511-6515, (2009).
Grimster, N, et al. Palladium-Catalyzed Intermolecular Alkenylation of Indoles by Solvent-Controlled Regioselective C-H Functionalization, Angew Chem. Int., vol. 44, pp. 3125-3129, (2005).
Parsons, R. et al. Total Syntheses of Strychnan and Aspiodospermatan-Type Alkaloids. 2. Generation of 15-(3-Furanyl) ABCE Teracyclic Intermediates, J. Org. Chem, vol. 58, pp. 7482-7489., (1993).
Udo, F, et al., Synthese von 3-(2-Indolyl)-acrylsaurederivaten, Arch. Pharm, (Weinheim), 310, pp. 975-979, (1977).
Bihovsky R et al, Synthesis of Cystamidin A (Pyrrole-3-Propanamide),A Reported Calpain Inhibitor, Bioorganic & Medicinal Chemistry Letters, vol. 6, No. 13, pp. 1541-1542, (1996).

\* cited by examiner

PAIN RELIEF COMPOUNDS

The present invention relates to compounds for the use in the treatment or prevention of pain in mammals, notably in humans, as well as a method for preparing these compounds.

Analgesics used today are old products and several of them date from the 19th century. Morphine is the reference analgesic for pains by nociception excesses.

However, morphine may be at the origin of multiple undesirable effects such as sleepiness, respiratory depression, nauseas, vomiting, convulsions, miosis, constipation or further dry mouth feeling.

Thus, the discovering of new anti-pain agents with at least equivalent effectiveness or even superior than morphine and without any undesirable effects is a major research objective for many teams worldwide.

Document WO 2011/033241 describes the use of potassium channel activators, notably TREK channels, as analgesic agents. However, the document does not give any indications for the compounds that may exhibit such an activity.

Cinnamyl 3,4-dihydroxy-α-cyanocinnamate or CDC, as well as its potential use as neuro- or cardio-protective agents, was described as an activator of TREK-1 channels (Sanjay et al., Mol. Pharmacol., 2004, 65, 599-610). However this document does not describe any analgesic activity of CDC.

Thus, a first object of the invention consists of proposing anti-pain compounds which get rid of the drawbacks of the state of the art and which provide a solution to all or part of the problems of the state of the art.

Another object is to propose anti-pain compounds for which the effectiveness for treating pain, notably pains by nociception excesses, is equivalent to, or even superior than the presently available compounds, notably morphine, while suppressing or limiting the risks of undesirable effects.

Another object of the invention is to propose anti-pain compounds which may be combined with other anti-pain agents, such as morphine, thereby reducing the risks of secondary effects related to their use.

The object of the invention is a compound of formula (A):

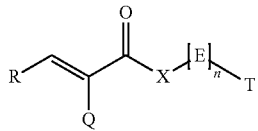

(A)

wherein:
R represents:
  a saturated, partially or totally unsaturated, aromatic or non-aromatic, substituted or non-substituted, 5-, 6- or 7-membered carbocycle;
  a saturated, partially or totally unsaturated, aromatic or non-aromatic, substituted or non-substituted, 5-, 6- or 7-membered heterocycle;
  a saturated, partially or totally unsaturated, aromatic or non-aromatic, substituted or non-substituted, 9-, 10-, 11-, 12-, 13- or 14-membered condensed carbocycle;
  a saturated, partially or totally unsaturated, aromatic or non-aromatic, substituted or non-substituted, 9-, 10-, 11-, 12-, 13- or 14-membered condensed heterocycle;

Q represents a hydrogen atom, a halogen, a $C_1$-$C_6$ alkyl group, a $C_1$-$C_6$ alkyl-amine group, a —CN, —$NR^1R^2$, —C(O)$OR^1$, a —$NR^3C(O)OR^4$ group;

Q, R and the carbon atoms to which they are bounded, form a saturated, partially or totally unsaturated, aromatic or non-aromatic, substituted or non-substituted, carbocycle, heterocycle, 5-, 6-, 7-, 8-, 9-, 10-, 11-, 12-, 13- or 14-membered condensed carbocycle or, 5-, 6-, 7-, 8-, 9-, 10-, 11-, 12-, 13- or 14-membered condensed heterocycle;

X represents O, —$CH_2$, S, $NR^1$;
E, identical or different, represents a group —$CHG^1$;
n represents 0, 1, 2 or 3;
T represents:
  a hydrogen atom;
  a substituted or non-substituted, branched or non-branched $C_1$-$C_{12}$ alkyl group;
  a group of formula -(L)$_m$-P(O)(O$T^1$)$_2$ wherein:
    L, identical or different, represents a group —$CHG^2$, O;
    m represents 0, 1, 2 or 3;
    $T^1$ represents an hydrogen atom, a $C_1$-$C_6$ alkyl group, a benzyl;
  a residue of an amino acid linked to its N-terminal position;
  an aryl group;
  a $C_1$-$C_6$ alkyl-aryl group;
  a $C_1$-$C_6$ alkyl-heterocycle group;
  a $C_2$-$C_6$ alkenyl-aryl group;
  a $C_2$-$C_6$ alkenyl-heterocycle group;
  a $C_2$-$C_6$ alkynyl-aryl group;
  a $C_2$-$C_6$ alkynyl-heterocycle group;
  a saturated or partially unsaturated, non-aromatic, substituted or non-substituted, 5- or 6-membered carbocycle;
  a saturated, partially or totally unsaturated, aromatic or non-aromatic, substituted or non-substituted, 5- or 6-membered heterocycle;
  a saturated, partially or totally unsaturated, aromatic or non-aromatic, substituted or non-substituted, 8-, 9- or 10-membered condensed heterocycle;

$R^1$ represents a hydrogen atom, a $C_1$-$C_6$ alkyl group;
$R^2$ represents a hydrogen atom, a $C_1$-$C_6$ alkyl group, —OH;
$R^3$ represents a hydrogen atom, a $C_1$-$C_6$ alkyl group;
$R^4$ represents a hydrogen atom, a $C_1$-$C_6$ alkyl group, a $C_1$-$C_6$ alkyl-aryl group;
$G^1$ represents a hydrogen atom, a $C_1$-$C_6$ alkyl group, —OH, a group of formula -($L^1$)$_q$-P(O)(O$R^7$)$_2$ wherein:
  $L^1$, identical or different, represents O, S, $CHR^8$, —$NR^8$;
  q represents 0, 1, 2, 3, 4, 5 or 6;
  $R^7$ and $R^8$ independently represent a hydrogen atom or a $C_1$-$C_6$ alkyl group, a benzyl;
$G^2$ represents a hydrogen atom, a $C_1$-$C_6$ alkyl group, —OH, a benzyl;

as well as an isomer or a pharmaceutically acceptable salt of this compound, for the use for the treatment and/or the prevention of pain
excluding
i) cinnamyl 3-4-dihydroxy-α-cyanocinnamate (CDC),
ii) ethyl 3-4-dihydroxy-α-cyanocinnamate (EDHBCA),
iii) 2-ethylthiophenyl 3-4-dihydroxy-α-cyanocinnamate (TEDHBCA),
iv) N-(3'-phenylpropyl)-3,4-dihydroxybenzylidenecyanoacetamide (Tyrphostin B46),
v) 1-carboxy-1-cyano-2(3,4-dihydroxyphenyl)ethylene, vi) 1-carboxy-1-cyano-2-phenylethylene,
vii) 1-carboxy-1-carboxy-2(4-hydroxyphenyl)ethylene,
viii) 1-carboxy-1-cyano-2(3,4-dihydroxyphenyl)ethylene,
ix) 1-carboxy-1-cyano-2(4,5-dihydroxyphenyl)ethylene,
x) 1-carboxy-1-cyano-2(4-methoxyphenyl)ethylene,
xi) 1-carboxy-1-cyano-2(4-fluorophenyl)ethylene,
xii) 1-carboxy-1-cyano-2(4-chlorophenyl)ethylene,
xiii) 1-carboxy-1-cyano-2(4-hydroxy-3,5-methoxyphenyl) ethylene,
xiv) 1-carboxy-1-cyano-2(4-hydroxyphenyl)ethylene,
xv) 1-carboxy-1-cyano-2(4-formylphenyl)ethylene
xvi) 1-carboxy-2(4-hydroxyphenyl)ethylene,
xvii) compound of formula

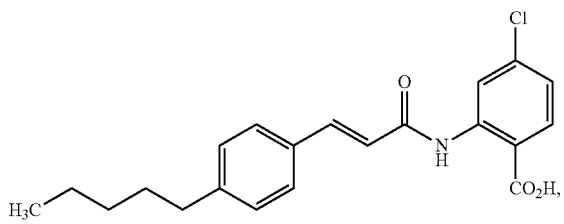 [SMILES: CCCCCc1ccc(/C=C/C(=O)Nc2cc(Cl)ccc2C(=O)O)cc1]

xviii) compound of formula

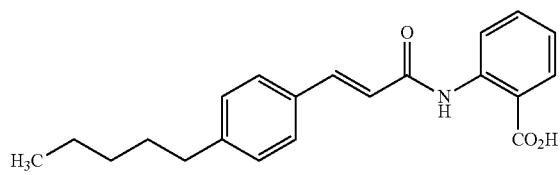 [SMILES: CCCCCc1ccc(/C=C/C(=O)Nc2ccccc2C(=O)O)cc1]

xix) compound of formula

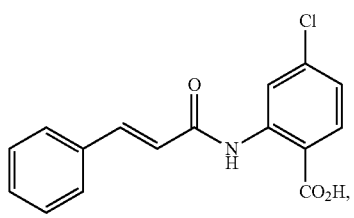 [SMILES: O=C(/C=C/c1ccccc1)Nc1cc(Cl)ccc1C(=O)O]

xx) 2-ethoxybenzene 3-4-dihydroxy-α-cinnamate (CAPE),
xxi) 3-(3,4-dihydroxyphenyl)-2-propenoic acid,
xxii) methyl 3-(3,4-dihydroxyphenyl)-2-propenoate,
xxii i) ethyl 3-(3,4-dihydroxyphenyl)-2-propenoate,
xxiv) lauryl 3-(3,4-dihydroxyphenyl)-2-propenoate,
xxv) tent-butyl 3-(3,4-di hydroxyphenyl)-2-propenoate,
xxvi) iso-pentyl 3-(3,4-dihydroxyphenyl)-2-propenoate,
xxvii) butyl 3-(3,4-dihydroxyphenyl)-2-propenoate,
xxviii) octanyl3-(3,4-dihydroxyphenyl)-2-propenoate,
xxix) iso-propyl 3-(3,4-dihydroxyphenyl)-2-propenoate,
xxx) iso-butyl 3-(3,4-dihydroxyphenyl)-2-propenoate,
xxxi) benzyl 3-(3,4-dihydroxyphenyl)-2-propenoate,
xxxii) phenethyl3-(3,4-dihydroxyphenyl)-2-propenoate.

Advantageously, R represents:
a saturated, partially or totally unsaturated, aromatic or non-aromatic, substituted or non-substituted, 5- or 6-membered carbocycle;
a saturated, partially or totally unsaturated, aromatic or non-aromatic, substituted or non-substituted, 5- or 6-membered heterocycle;
a saturated, partially or totally unsaturated, aromatic or non-aromatic, substituted or non-substituted, 9- or 10-membered condensed carbocycle;
a saturated, partially or totally unsaturated, aromatic or non-aromatic, substituted or non-substituted, 9- or 10-membered condensed heterocycle.

Also advantageously, Q, R and the carbon atoms to which they are bounded, form a saturated, partially or totally unsaturated, aromatic or non-aromatic, substituted or non-substituted, carbocycle, heterocycle, 5-, 6-, 7-, 8-, 9- or 10-membered condensed carbocycle or 5-, 6-, 7-, 8-, 9- or 10-membered condensed heterocycle.

Advantageously, T represents:
a residue of an amino acid, linked by its N-terminal position and selected from the group consisting of cysteine, glycine, lysine, phenylalanine and serine,
a group of formula $-(L)_m-P(O)(OT^1)_2$ wherein:
L, different from each other, represent a group $—CHG^2$ and a group O with $G^2$ represents a hydrogen atom;
m represents 2;
$T^1$ represents a hydrogen atom;
a group of formula $-(L)_m-P(O)(OT^1)_2$ wherein:
L, different from each other, represent a group $—CHG^2$ and a group O with $G^2$ represents a hydrogen atom;
m represents 2;
$T^1$ represents a benzyl;
Advantageously, $G^1$ represents a group of formula $-(L^1)_q-P(O)(OR^7)_2$ wherein:
$L^1$, different from each other, represent O and $CHR^8$;
q represents 2;
$R^7$ represents a hydrogen atom or a $C_1$-$C_6$ alkyl, a benzyl;
$R^8$ represents a hydrogen atom.

According to the invention, the compound may be a compound of formula (A), excluding
i) a compound of formula

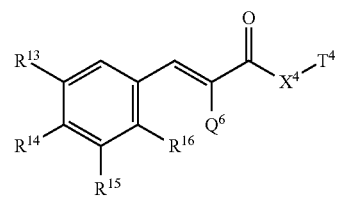

wherein
$Q^6$ represents H, —CN, —COOH
$X^4$ represents O
$T^4$ represents H
$R^{13}$ represents H, —OH, $C_1$-$C_2$alkoxy,
$R^{14}$ represents H, —OH, $C_1$-$C_2$alkoxy, —NO$_2$, tert-butyl, iso-proline, —CH$_2$SMe, —OCH, —F, —Cl,
$R^{15}$ represents H, —OH, $C_1$alkoxy, —NO$_2$, tert-butyl, iso-proline, —CH$_2$SPh, —CH$_2$SMe,
$R^{16}$ represents H, —OH,
ii) compound of formula

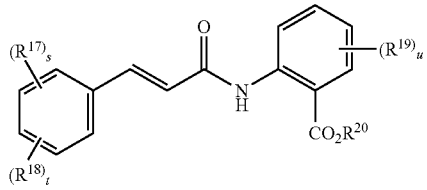

wherein
$R^{17}$ represents a halogen, —CF$_3$, —NO$_2$, —NH$_2$, —CN,
$R^{18}$ h represents $C_1$-$C_8$ alkyl, $C_2$-$C_8$ alkenyl, $C_1$-$C_8$ alkoxy, —NH—(C$_1$-C$_8$)alkyl, —C(O)—(C$_1$-C$_8$)alkyl, —O—C(O)—(C$_1$-C$_8$)alkyl, —CO$_2$—(C$_1$-C$_8$)alkyl, —C(O)—NH—(C$_1$-C$_8$)alkyl, —NH—C(O)—(C$_1$-C$_8$)

alkyl, with the $C_1$-$C_8$ alkyl and the $C_2$-$C_8$ alkenyl groups which may be branched or non-branched and may be optionally substituted with at least one group selected from a halogen, a lower alkoxy, —$NH_2$, —NH—(lower alkyl), —N-(lower alkyl)$_2$, cycloalkyl, aryl and a heterocycle, $R^{19}$ represents a halogen, a lower alkyl, a lower alkoxy, —$NH_2$, —NH-(lower alkyl), —N-(lower alkyl)$_2$, —$CF_3$, —$NO_2$, —CN, $R^{20}$ represents a hydrogen or lower alkyl, s represents an integer ranging from 0 to 2, t represents an integer ranging from 1 to 2, u represents an integer ranging from 0 to 2.

According to the invention, the compound may be a compound of formulae (A1), (A2), (A3) and (A4)

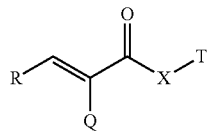
(A1)

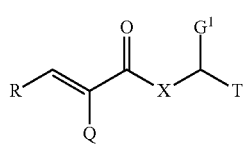
(A2)

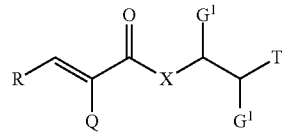
(A3)

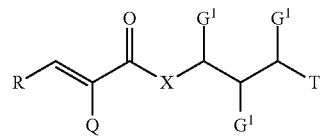
(A4)

wherein R, Q, X, T, $T^1$, $R^1$, $R^2$, $R^3$, $R^4$, $R^7$, $R^8$, $G^1$, $G^2$, L and $L^1$ are as defined for the compound of formula (A).

According to the invention, the compound may be chosen amongst the compounds of formulae (1a), (1b), (1c), (1d), (1e), (2a), (2b), (2c), (2d), (2e), (3a), (3b), (3c), (3d), (3e), (4a), (4b), (4c), (4d) or (4e):

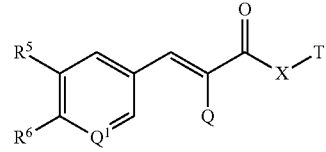
(1a)

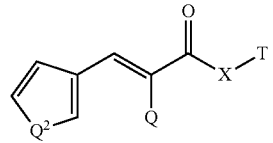
(1b)

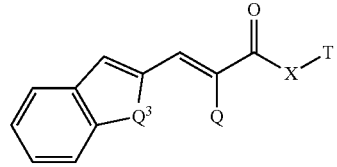
(1c)

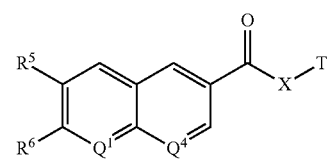
(1d)

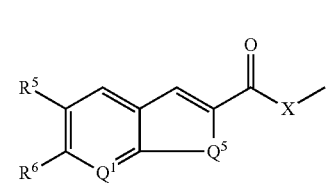
(1e)

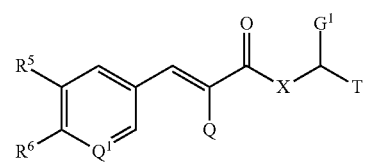
(2a)

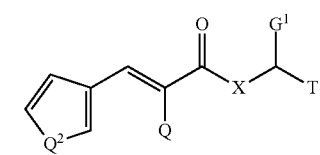
(2b)

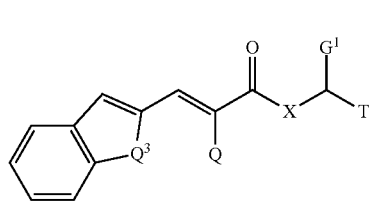
(2c)

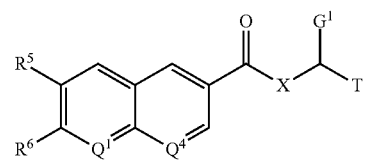
(2d)

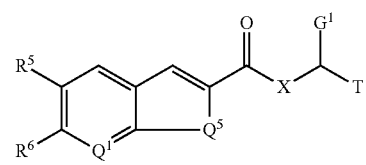
(2e)

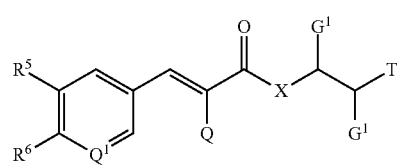
(3a)

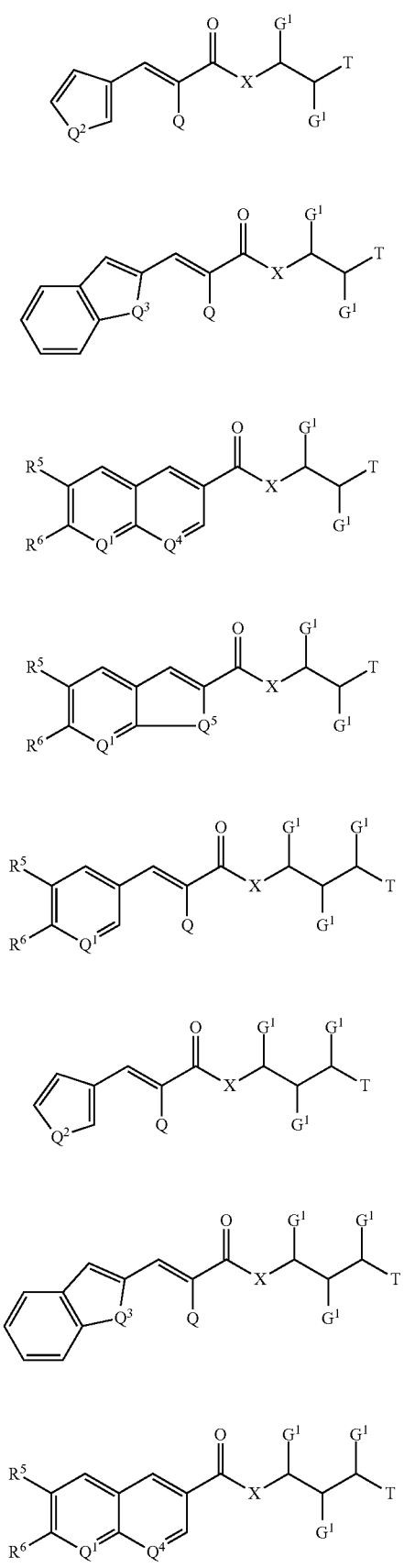

wherein:
X and T are as defined for the compound of formula (A);
Q represents a hydrogen atom, a halogen, a $C_1$-$C_6$ alkyl group, a $C_1$-$C_6$ alkyl-amine group, —CN, $NR^1R^2$, —C(O)$OR^1$;
$Q^1$ represents $CR^1$, N, $NH^+Z^-$, $NH_3^+Z^-$ wherein $Z^-$ independently represents a halide ion, a carboxylate ion;
$Q^2$ and $Q^3$ independently represent —$CR^9R^{10}$, O, S, $NR^1$;
$Q^4$ represents N, $NH^+Z^-$;
$Q^5$ represents O, S, $NR^1$;
$R^1$, $R^9$ and $R^{10}$ independently represent a hydrogen atom, a $C_1$-$C_6$ alkyl group;
$R^2$, identical or different, represents a hydrogen atom, a $C_1$-$C_6$ alkyl group, —OH;
$R^5$ and $R^6$ independently represent a hydrogen atom, a $C_1$-$C_6$ alkyl group, a halogen, —OH, a $C_1$-$C_6$ alkoxy group, —$NH_2$, —$NO_2$, a group of formula -($L^3$)$_v$-[P(O)($OR^{21}$)$_2$]$_w$, wherein:
$L^3$, identical or different, represents O, S, $CHR^{22}$, —$NR^{22}$;
v represents 0, 1, 2, 3, 4, 5 or 6;
w represents 1 or 2;
$R^{21}$ and $R^{22}$ independently represent a hydrogen atom, a $C_1$-$C_6$ alkyl group, a benzyl;
$G^1$, identical or different, represents a hydrogen atom, a $C_1$-$C_6$ alkyl group, —OH, 2 adjacent $G^1$ groups and the carbon atoms to which they are bounded, form an epoxide ring, a group of formula —$X^2$-($L^1$)$_q$—P(O)($OR^7$)$_2$ wherein:
$L^1$, identical or different, represents O, S, $CHR^8$, —$NR^8$;
q represents 0, 1, 2, 3, 4, 5 or 6;
$R^7$ and $R^8$ independently represent a hydrogen atom, a $C_1$-$C_6$ alkyl group, a benzyl;
$G^2$, identical or different, represents a hydrogen atom, a $C_1$-$C_6$ alkyl group, —OH, a benzyl.
Advantageously, $R^9$ and $R^{10}$ represent a hydrogen atom.
According to the invention, the compound may be chosen amongst the compounds of formulae (1a), (2a), (3a) or (4a) wherein:
Q represents a hydrogen atom, —CN, —$CH_2NH_3^+Z^-$, —C(O)OH, —F;
$Q^1$ represents —CH, $NH^+Z^-$;
$Z^-$ represents $Cl^-$, $TFA^-$;
X represents O, NH;
T represents:
a hydrogen atom;
a methyl group;
an ethyl group;
a tert-butyl group;
an iso-pentyl group;
a lauryl group;
a group of formula -(L)$_m$-P(O)($OT^1$)$_2$ wherein:
L, identical or different, represents a group —$CHG^2$;
m represents 0, 1, 2 or 3;
$T^1$ represents a hydrogen atom, a methyl, an ethyl, a benzyl;

a residue of an amino acid, linked by its N-terminal position and selected from the group consisting of cysteine, glycine, lysine, phenylalanine and serine;
a phenyl group;
a cyclohexyl group;
a group

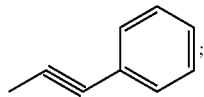

a group

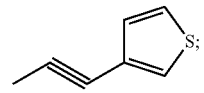

an indole group;
$G^1$, identical or different, represents a hydrogen atom, an ethyl group, —OH, 2 adjacent $G^1$ groups and the carbon atoms to which they are bounded, form an epoxide ring, a group of formula $-(L^1)_q-P(O)(OR^7)_2$ wherein:
  $L^1$, identical or different, represents O, S, $CHR^8$, $—NR^8$;
  q represents 0, 1, 2, 3, 4, 5 or 6;
  $R^7$ and $R^8$ independently represent a hydrogen atom, a methyl group, an ethyl group, a benzyl;
$G^2$, identical or different, represents a hydrogen atom $C_1$-$C_6$ alkyl group, —OH, a benzyl;
$R^5$ and $R^6$ independently represent a hydrogen atom, a $C_1$-$C_6$ alkyl group, a halogen, —OH, a $C_1$-$C_6$ alkoxy group, —$NH_2$, —$NO_2$, a group of formula $-(L_2)_v-[P(O)(OR^{21})_2]_w$ wherein:
  $L^3$, identical or different, represents a group —$CHR^{22}$, O;
  v represents 0 or 1;
  w represents 1 or 2;
  $R^{21}$ and $R^{22}$ independently represent a hydrogen atom, a methyl, an ethyl, a benzyl.

According to the invention, the compound may be a compound of formula (1a) wherein:
Q represents a hydrogen atom, —CN, —$CH_2NH_3^+TFA^-$, —C(O)OH, —F;
$Q^1$ represents —CH, $NH^+TFA^-$;
X represents O or NH;
T represents a hydrogen atom, a methyl group, an ethyl group, a tert-butyl group, an iso-pentyl group, a lauryl group, a cyclohexyl group, a residue of an amino acid linked by its N-terminal position and selected in the group consisting of cysteine, glycine, lysine, phenylalanine and serine, a group of formula $-(L)_m-P(O)(OT^1)_2$ wherein:
  L, identical or different, represents a group —$CHG^2$, O;
  m represents 0, 1, 2 or 3;
  $T^1$ represents a hydrogen atom, a methyl, an ethyl, a benzyl;
$R^5$ and $R^6$ independently represent a hydrogen atom, a $C_1$-$C_6$ alkyl group, a halogen, —OH, a $C_1$-$C_6$ alkoxy group, —$NH_2$, —$NO_2$, a group of formula $-(L^3)_v-[P(O)(OR^{21})_2]_w$ wherein:
  $L^3$, identical or different, represents a group —$CHR^{22}$, O;
  v represents 0 or 1;
  w represents 1 or 2;
  $R^{21}$ and $R^{22}$ independently represent a hydrogen atom, a methyl, an ethyl, a benzyl;
$G^2$, identical or different, represents a hydrogen atom, a methyl, an ethyl, —OH, a benzyl.

According to the invention, the compound may be a compound of formula (2a) wherein:
Q represents a hydrogen atom, —CN;
$Q^1$ represents —CH;
X represents O;
T represents:
  a group of formula $-(L)_m-P(O)(OT^1)_2$ wherein:
    L represents O;
    m represents 1;
    $T^1$ represents a hydrogen, a methyl, an ethyl, a benzyl;
  a group

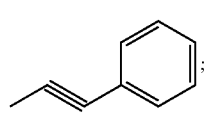

a group

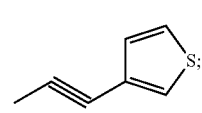

an indole group;
$G^1$ represents a hydrogen atom, a methyl, an ethyl, —OH, a group of formula $-(L^1)_q-P(O)(OR^7)_2$ wherein:
  $L^1$, identical or different, represents O, $CHR^8$;
  q represents 0, 1, 2, 3, 4, 5 or 6;
  $R^7$ and $R^8$ independently represent a hydrogen, a methyl, an ethyl or a benzyl;
$R^5$ and $R^6$ independently represent a hydrogen atom, a $C_1$-$C_6$ alkyl group, an halogen, —OH, a group of formula $-(L^3)_v-[P(O)(OR^{21})_2]_w$ wherein:
  $L^3$, identical or different, represents a group $CHR^{22}$, O;
  v represents 0 or 1;
  w represents 1 or 2;
  $R^{21}$ and $R^{22}$ independently represent a hydrogen atom, a methyl, an ethyl, a benzyl.

According to the invention, the compound may be a compound of formula (3a) wherein:
Q represents —CN;
$Q^1$ represents —CH;
X represents O;
T represents a phenyl group;
$G^1$ represents a hydrogen atom, —OH, 2 adjacent $G^1$ groups and the carbon atoms to which they are bounded, form an epoxide ring;
$R^5$ and $R^6$ represent OH.

According to the invention, the compound may be a compound of formula (4a) wherein:
Q represents —CN;
$Q^1$ represents —CH;
X represents O;
T represents a phenyl group;
$G^1$ represents a hydrogen atom, —OH, 2 adjacent $G^1$ groups and the carbon atoms to which they are bounded, form an epoxide ring;
$R^5$ and $R^6$ represent OH.

Advantageously, the compound according to the invention is chosen amongst the compounds of formulae (1a1) to (1a20), (2a1) to (2a3), (3a1), (4a1) or (4a2):

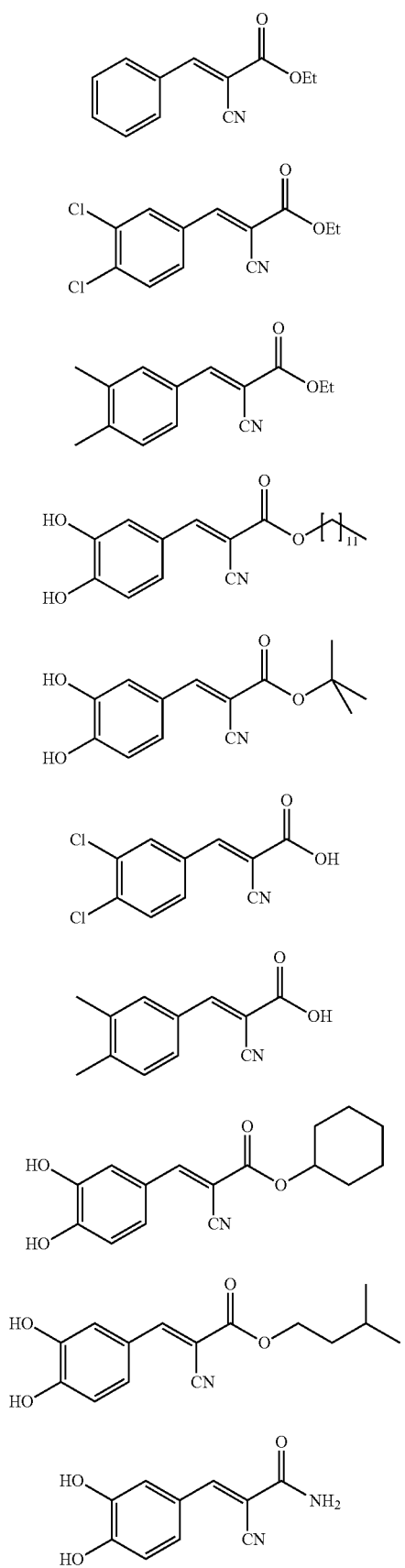
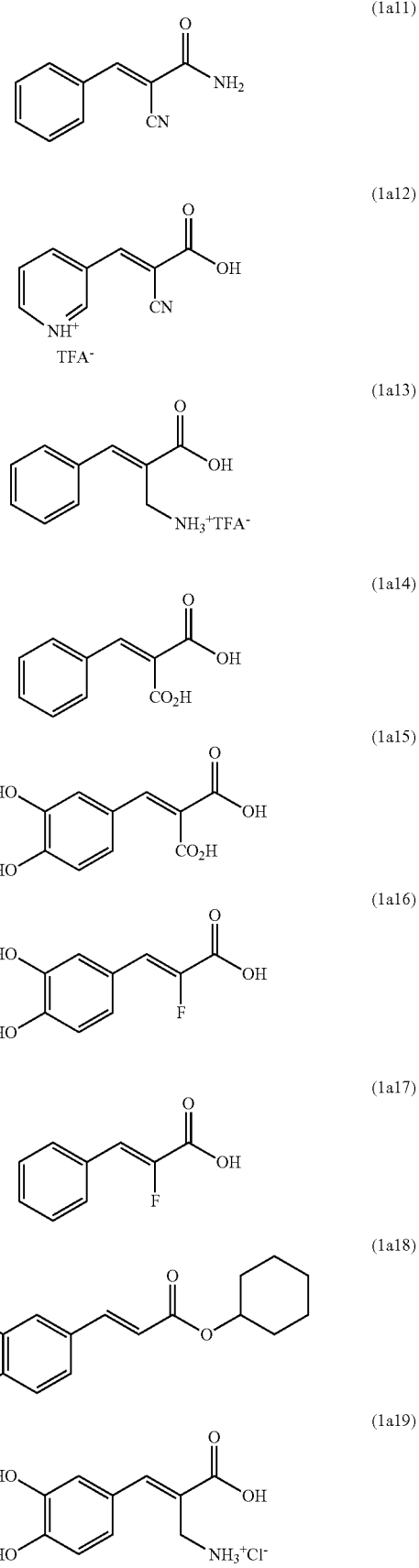

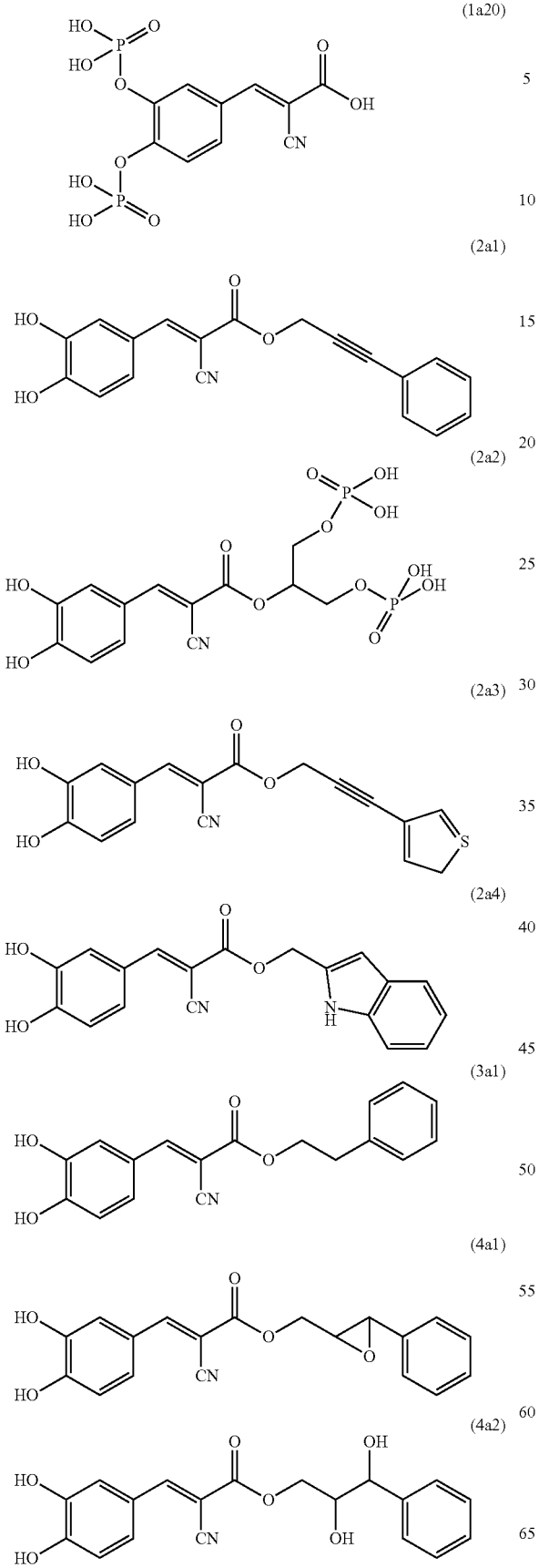

According to the invention, the compound according to the invention is chosen amongst the compounds of formulae (1b), (2b), (3b) or (4b) wherein:
  Q represents —CN, —C(O)OH, —F, —CH$_2$NH$_3$$^+$Z$^-$, wherein Z$^-$ independently represents Cl$^-$ or TFA$^-$;
  Q$^2$ represents —CR$^9$R$^{10}$, O, S;
  X represents O or NH;
  T represents:
    a hydrogen atom;
    a methyl group;
    an ethyl group;
    a propyl or isopropyl group,
    a butyl or tert-butyl group;
    a phenyl group;
    a group

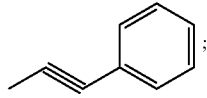

a group

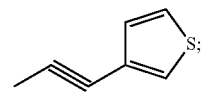

an indole group;
  G$^1$ represents a hydrogen atom, an ethyl group, —OH, 2 adjacent G$^1$ groups and the carbon atoms to which they are bounded, form an epoxide ring;
  R$^9$ and R$^{10}$ independently represent a hydrogen atom, a C$_1$-C$_6$ alkyl group.

According to the invention, the compound may be a compound of formula (1b) wherein:
  Q represents —CN, —CH$_2$NH$_3$$^+$TFA$^-$;
  Q$^2$ represents O, S;
  X represents O;
  T represents a hydrogen atom.

Advantageously, the compound is chosen amongst the compounds of formulae (1b1), (1b2), (1b3) and (1b4)

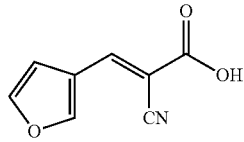

(1b1)

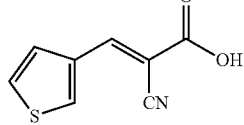

(1b2)

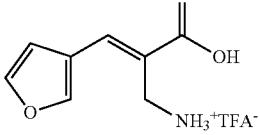

(1b3)

-continued

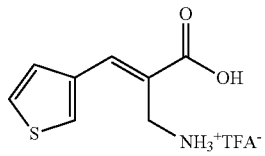
(1b4)

According to the invention, the compound may be selected from the compounds of formulae (1c), (2c), (3c) or (4c) wherein:
Q represents —CN, —CH$_2$NH$_3{}^+$Z$^-$, —C(O)OH, —F;
Q$^3$ represents —CR$^9$R$^{10}$, O, S;
Z$^-$ is selected from Cl$^-$ or TFA$^-$;
X represents O or NH;
T represents:
  a hydrogen atom;
  a methyl group;
  an ethyl group;
  a propyl or isopropyl group,
  a butyl or tert-butyl group;
  a phenyl group;
  a group

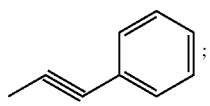;

a group

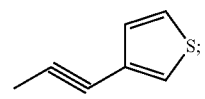;

an indole group;
G$^1$ represents a hydrogen atom, an ethyl group, —OH, 2 adjacent G$^1$ groups and the carbon atoms to which they are bounded, form an epoxide ring;
R$^9$ and R$^{10}$ independently represent a hydrogen atom, a C$_1$-C$_6$ alkyl group.

According to the invention, the compound may be a compound of formula (1c) wherein:
Q represents —CN;
Q$^2$ represents —NH;
X represents O;
T represents a hydrogen atom.

Advantageously, the compound is a compound of formula (1c1)

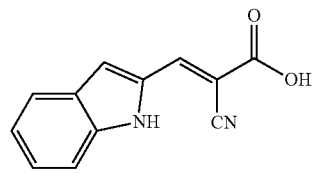
(1c1)

According to the invention, the compound may be selected from the compounds of formulae (1d) or (1e) wherein:
X represents O, —CH$_2$, S, NR$^1$;
Q$^1$ represents —CH, N, NH$^+$Z$^-$;
Q$^4$ represents N, NH$^+$Z$^-$;
Z$^-$ independently represents Cl$^-$ or TFA$^-$;
T represents a hydrogen atom, an ethyl group;
R$^5$ and R$^6$ represent —OH.

Advantageously, the compound is selected from the compounds of formulae (1d1) or (1e1)

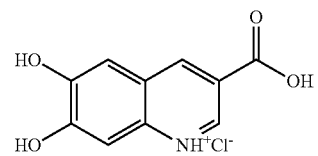
(1d1)

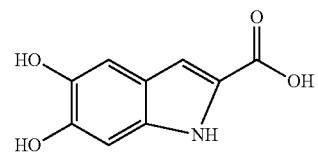
(1e1)

The invention also concerns a method for preparing a compound of formula (A) comprising:
(i) the preparation of a compound of formula (E) by the reaction between a compound of formula (C) and a compound of formula (D),

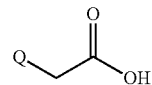
(C)

(D)

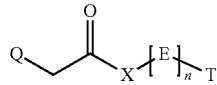
(E)

wherein Q, X, E, T and n are as defined for the compound of formula (A);
(ii) the reaction of a compound of formula (E) with a compound of formula RCHO wherein R is as defined for the compound of formula (A), in order to form the compound of formula (A).

According to the invention, the step (i) may consist of reacting an acid of formula (C) (1 eq) and a compound of formula (D) (1.1 eq) in anhydrous dichloromethane, N,N'-dicyclohexylcarbodiimide (DCC) or 3-(diethoxyphosphoryloxy)-1,2,3-benzotriazin-4(3H)-one (DEPBT) and N,N-dimethylaminopyridine (DMAP) or N,N-disopropylethylarnine (DIPEA) at 0° C. The formed precipitate is then filtered and the filtrate is evaporated in vacuum. The residue is purified by chromatography and the compound of formula (E) is obtained.

According to the invention, the step (ii) may consist of coupling the compound of formula (E) with an aldehyde of formula RCHO in the presence of piperidine in anhydrous dichloromethane. The mixture is washed with an aqueous solution saturated with ammonium chloride and the organic phase is extracted with ethyl acetate, dried and filtered. The organic residue is purified on silica in order to obtain the compound of formula (A).

In another embodiment of the invention, step (ii) may consist of reacting a phosphonate solution of formula (E) in anhydrous tetrahydrofurane in the presence of sodium hydride at 0° C. The aldehyde of formula RCHO is added after 30 minutes. The organic mixture is extracted with ethyl acetate, dried and filtered. The residue is purified by chromatography in order to obtain the compound of formula (A).

According to the invention, the compound according to the invention is used in the treatment or the prevention of acute pains, pains by excessive nociceptive stimulations, chronic pains, neuropathic pains, visceral pains, cancer pains, pains by the dysfunction of the sympathetic system or psychic pains.

By acute pains, are meant pains triggering reactions, the finality of which is to reduce the cause thereof and to limit the consequences thereof. Acute pains are mainly short pains and only last a few seconds. Mention may notably be made for example of pains subsequent to the contact of the skin with fire or subsequent to an insect sting.

By pains by excess of nociceptive stimulations, are meant those stemming from the stimulation of nociceptors by substances released by damaged or inflamed tissues, these substances notably including extracellular protons, nucleotides, nerve growth factors, serotonin or further bradykinin. They mainly result from lesions of peripheral tissues, thereby causing an excess of painful influxes transmitted by the nervous system.

By chronic pains, are meant pains, the duration of which may be of several months, or even of several years. They may accompany inflammatory or neuropathic pathologies.

By neuropathic pains, are meant pains related to peripheral or central lesions. These pains are related to malfunction of the mechanisms for controlling nociceptive messages and may be classified according to 2 types:
    peripheral neuropathic pains may be caused by medicinal treatment, for example by alkaloids of periwinkle (vinorelbine) used in the treatment of cancers.
    central neuropathic pains caused by spinal or traumatic damages, for example a lesion at the brain.
These pains may last for a long time after the repairing of the damaged tissues and may therefore become chronic pains.

By visceral pains, are meant pains essentially with a hypernociceptive nature, which may originate in the skin area. They may be accompanied by hyperalgesia of the skin and of the deep tissues, by tonic muscular contractions and intense emotional reactions.

By cancer pains, are meant the pains which develop in a cancer context, associating both a nociception excess related to cancer development and a neuropathic component, related to dysfunction of the peripheral nervous system consecutive to lesional invasion or to treatments.

By pains by dysfunction of the sympathetic system, are meant pains expressed both as an excess of nociception, of signs suggestive of a neuropathic component but also of sympathetic perturbations.

By psychical pains, are meant pains accompanying mental pathologies, such as for example depression or schizophrenia.

Within the scope of the present invention, the compound of formula (A) may be incorporated into a pharmaceutical composition.

Thus, the object of the invention is also a pharmaceutical composition comprising a compound of formula (A) and at least one pharmaceutically acceptable carrier.

The whole of the characteristics or preferences shown for the compound of formula (A) also apply to the composition according to the invention.

By pharmaceutically acceptable carrier, is meant any solvent, dispersion medium or additives which does not produce any secondary reaction, for example an allergic reaction, in humans or in animals. The pharmaceutically acceptable carrier may notably be selected according to the administration route, for example an oral, sub-lingual, nasal, buccal, rectal or parenteral route (i.e. intravenous, subcutaneous, intra-dermal or intra-muscular route). The pharmaceutically acceptable carrier is preferentially selected for an oral or parenteral administration route.

The dose depends on factors such as the administration method, the nature of the pain, the age, the weight and the health condition of the patient.

Another aspect of the invention relates to a kit comprising:
    a first composition comprising a compound of formula (A),
    a second composition comprising an anti-pain agent.

The whole of the characteristics or preferences shown for the compound of formula (A) also applies to the kit according to the invention.

The anti-pain agents used in the kit according to the invention may be selected from analgesic agents of level 1 to 3 according to the classification of the World Health Organization.

Analgesics of level 1 are peripheral analgesics against weak or moderate pains, such as paracetamol, aspirin, or non-steroidal anti-inflammatories.

Analgesics of level 2 are weak central analgesics against moderate to severe pains, which may correspond to associations between analgesics of level 1 and weaker opioid analgesics, such as tradamol.

Analgesics of level 3 are strong central analgesics against very severe and stubborn pains, such as strong opioids (morphine, pethadine, dextromoramide) and antagonists (pentazocine, nalbuphine).

According to the invention, the compositions may be administered at the same time, simultaneously or extemporaneously to the patient.

Thus, the use of the kit according to the invention gives the possibility of obtaining an equivalent anti-pain effectiveness, or even greater than the one obtained by isolated administration of the anti-pain agent, while reducing the risks of secondary effects relating to their use.

The object of the invention is also a compound of formula (B)

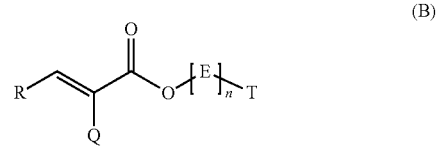

wherein:
    R represents
        a saturated, partially or totally unsaturated, aromatic or non-aromatic, substituted or non-substituted, 5-, 6- or 7-membrered carbocycle;
        a saturated, partially or totally unsaturated, aromatic or non-aromatic, substituted or non-substituted, 5-, 6- or 7-membrered heterocycle;
        a saturated, partially or totally unsaturated, aromatic or non-aromatic, substituted or non-substituted, 9-, 10-, 11-, 12-, 13- or 14-membrered condensed carbocycle;
        a saturated, partially or totally unsaturated, aromatic or non-aromatic, substituted or non-substituted, 9-, 10-, 11-, 12-, 13- or 14-membrered condensed heterocycle;

Q represents a hydrogen atom, —CN, —NR$^1$R$^2$, C$_1$-C$_2$ alkyl-amine group;

X represents O, —NH;

E, identical or different, represents a —CHG$^1$ group;

n represents 0 or 1;

T represents:
- a hydrogen atom;
- a substituted or non-substituted, C$_2$-C$_4$ alkynyl-aryl group;
- a branched or non-branched, substituted or non-substituted, C$_1$-C$_{12}$ alkyl group;
- a group of formula -(L)$_m$-P(O)(OT$^1$)$_2$ wherein:
    L, identical or different, represents a —CHG$^2$ group, O;
    m represents 0, 1, 2 or 3;
    T$^1$ represents a hydrogen atom, a C$_1$-C$_6$ alkyl group, a benzyl;
- a residue of an amino acid linked by its N-terminal position;
- a saturated or partially unsaturated, non-aromatic, substituted or non-substituted, 5-, or 6-membered carbocycle;

G$^1$ represents a hydrogen atom, a C$_1$-C$_6$ alkyl group, —OH, a group of formula -(L$^1$)$_q$-P(O)(OR$^7$)$_2$ wherein:
    L$^1$, identical or different, represents O, S, CHR$^8$, —NR$^8$;
    q represents 0, 1, 2, 3, 4, 5 or 6;
    R$^7$ and R$^8$ independently represent a hydrogen atom, a C$_1$-C$_6$ alkyl group, a benzyl;

G$^2$ represents a hydrogen atom, a C$_1$-C$_6$ alkyl group, —OH, a benzyl;

R$^1$ represents a hydrogen atom, a C$_1$-C$_6$ alkyl group;

R$^2$ represents a hydrogen atom, a C$_1$-C$_6$ alkyl group, —OH;

as well as an isomer or a pharmaceutically acceptable salt of this compound; excluding i) compounds of formula (B) wherein R represents an aryl group, T represents a hydrogen atom, Q represents —CN and n represents 0, ii) cinnamyl 3-4-dihydroxy-α-cyanocinnamate (CDC), iii) 3-(3,4-dihydroxyphenyl)-2-propenaïc acid, iv) methyl 3-(3,4-dihydroxyphenyl)-2-propenoate, v) ethyl 3-(3,4-dihydroxyphenyl)-2-propenoate, vi) lauryl 3-(3,4-dihydroxyphenyl)-2-propenoate, vii) tert-butyl 3-(3,4-dihydroxyphenyl)-2-propenoate, viii) iso-pentyl 3-(3,4-dihydroxyphenyl)-2-propenoate, ix) butyl 3-(3,4-dihydroxyphenyl)-2-propenoate, x) octanyl 3-(3,4-dihydroxyphenyl)-2-propenoate, xi) iso-propyl 3-(3,4-dihydroxyphenyl)-2-propenoate, xii) iso-butyl 3-(3,4-dihydroxyphenyl)-2-propenoate, xiii) benzyl 3-(3,4-dihydroxyphenyl)-2-propenoate, xiv) phenethyl 3-(3,4-dihydroxyphenyl)-2-propenoate, xv) cyclohexyl 3-(3,4-dihydroxyphenyl)-2-propenoate, xvi) ethyl 3-4-dihydroxy-α-cyanocinnamate (EDHBCA), xvii) methyl 3-(4-nitrophenyl)-2-propenoate xviii) methyl 3-(4-chlorophenyl)-2-propenoate, xix) methyl 3-(4-bromophenyl)-2-propenoate, xx) methyl 3-phenyl-2-propenoate, xxi) methyl 3-(3-chlorophenyl)-2-propenoate.

According to the invention, the compound may be chosen amongst the compounds of formulae (B1), (B2), (B3), (B4) or (B5):

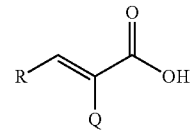
(B1)

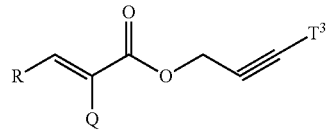
(B2)

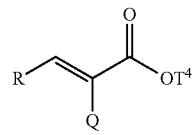
(B3)

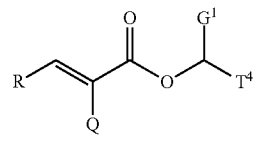
(B4)

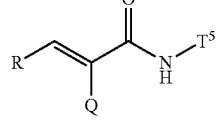
(B5)

wherein:

R represents:
- a saturated, partially or totally unsaturated, aromatic or non-aromatic, substituted or non-substituted, 5-, 6- or 7-membrered carbocycle;
- a saturated, partially or totally unsaturated, aromatic or non-aromatic, substituted or non-substituted, 5-, 6- or 7-membrered heterocycle;
- a saturated, partially or totally unsaturated, aromatic or non-aromatic, substituted or non-substituted, 9-, 10-, 11-, 12-, 13- or 14-membrered condensed carbocycle;
- a saturated, partially or totally unsaturated, aromatic or non-aromatic, substituted or non-substituted, 9-, 10-, 11-, 12-, 13- or 14-membrered condensed heterocycle;

Q represents:
- a hydrogen atom;
- CN;
- NR$^1$R$^2$;
- a C$_1$-C$_2$ alkyl-amine group;

T$^3$ represents a substituted or non-substituted aryl group;

T$^4$ represents:
- a branched or non-branched, substituted or non-substituted, C$_1$-C$_{12}$ alkyl group,
- a group of formula -(L)$_m$-P(O)(OT$^1$)$_2$ wherein:
    L, identical or different, represents a —CHG$^2$ group, O;
    m represents 0, 1, 2 or 3;
    T$^1$ represents a hydrogen atom, a C$_1$-C$_6$ alkyl group, a benzyl;
- a saturated or partially unsaturated, non-aromatic, substituted or non-substituted, 5- or 6-membered carbocyle;

$T^5$ represents a residue of an amino acid linked by its N-terminal position;

$G^1$ represents a hydrogen atom, a $C_1$-$C_6$ alkyl group, —OH, a group of formula -$(L^1)_q$-P(O)(OR$^7$)$_2$ wherein:
  $L^1$, identical or different, represents O, S, CHR$^8$, —NR$^8$;
  q represents 0, 1, 2, 3, 4, 5 or 6;
  $R^7$ and $R^8$ represent a hydrogen atom, a $C_1$-$C_6$ alkyl group, a benzyl;

$G^2$ represents a hydrogen atom, a $C_1$-$C_6$ alkyl group, —OH, a benzyl;

$R^1$ represents a hydrogen atom, a $C_1$-$C_6$ alkyl group;

$R^2$ represents a hydrogen atom, a $C_1$-$C_6$ alkyl group, —OH.

According to the invention, the compound may be a compound of formula (B1) wherein:
  R represents:
    a bis-hydroxyphenyl group;
    an indole group;
    a furane group;
  Q represents:
    CN;
    a group CH$_2$—NH$_3^+$Cl$^-$, NH$_3^+$Cl$^-$.

According to the invention, the compound may be a compound of formula (B2) wherein:
  R represents a bis-hydroxyphenyl group;
  Q represents CN;
  $T^3$ represents a phenyl group.

According to the invention, the compound may be a compound of formulae (B3a), (B4a) or (B5a)

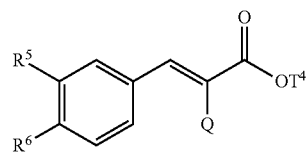
(B3a)

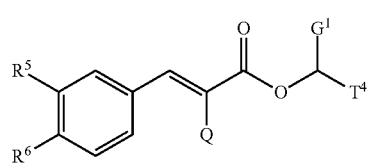
(B4a)

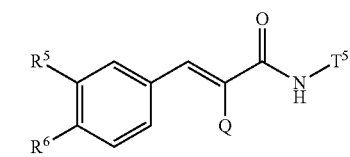
(B5a)

wherein:
  Q represents a hydrogen atom, —CN, —NR$^1$R$^2$, a $C_1$-$C_2$ alkyl-amine group;
  $T^4$ represents:
    a hydrogen atom;
    a branched or non-branched, substituted or non-substituted, $C_1$-$C_{12}$ alkyl group;
    a group of formula $(L)_m$-P(O)(OT$^1$)$_2$ wherein:
      L, identical or different, represents a —CHG$^2$ group, O;
      m represents 0, 1, 2 or 3;
      $T^1$ represents a hydrogen atom, a $C_1$-$C_6$ alkyl group, a benzyl;
      a saturated or partially unsaturated, non-aromatic, substituted or non-substituted 5- or 6-membered carbocycle;
      a residue of an amino acid linked by its N-terminal position;

$G^1$ represents a hydrogen atom, a $C_1$-$C_6$ alkyl group, —OH, a group of formula -$(L^1)_q$-P(O)(OR$^7$)$_2$ wherein:
  $L^1$, identical or different represents O, S, CHR$^8$, —NR$^8$;
  q represents 0, 1, 2, 3, 4, 5 or 6;
  $R^7$ and $R^8$ independently represent a hydrogen atom, a $C_1$-$C_6$ alkyl group, a benzyl;

$G^2$ represents a hydrogen atom, a $C_1$-$C_6$ alkyl group, —OH, a benzyl;

$R^5$ and $R^6$ independently represent a hydrogen atom, a $C_1$-$C_6$ alkyl group, a halogen, —OH, a $C_1$-$C_6$ alkoxy group, —NH$_2$, —NO$_2$, a group of formula -$(L^3)_v$-[P(O)(OR$^{21}$)$_2$]$_w$ wherein:
  $L^3$, identical or different represents O, S, CHR$^{22}$, —NR$^{22}$;
  v represents 0, 1, 2, 3, 4, 5 or 6;
  w represents 1 or 2
  $R^{21}$ and $R^{22}$ independently represent a hydrogen atom, a $C_1$-$C_6$ alkyl group, a benzyl;

$R^1$ represents a hydrogen atom, a $C_1$-$C_6$ alkyl group;

$R^2$ represents a hydrogen atom, a $C_1$-$C_6$ alkyl group, —OH.

According to the invention, the compound may be a compound of formula (B3a) wherein:
  Q represents a hydrogen atom, —CN, —NR$^1$R$^2$, a $C_1$-$C_2$ alkyl-amine group;
  $T^4$ represents:
    a hydrogen atom;
    a tert-butyl group;
    an iso-pentyl group;
    a lauryl group;
    a group of formula -$(L)_m$-P(O)(OT$^1$)$_2$ wherein:
      L, identical or different, represents a —CHG$^2$ group, O;
      m represents 0, 1, 2 or 3;
      $T^1$ represents a hydrogen atom, a methyl, an ethyl, a benzyl;
    a cyclohexyl group;
  $G^2$ represents a hydrogen atom, $C_1$-$C_6$ alkyl group, —OH, a group of formula -$(L^2)_r$-P(O)(OR$^{10}$)$_2$ wherein:
    $L^2$, identical or different, represents O, S, CHR$^{11}$, —NR$^{11}$;
    r represents 0, 1, 2, 3, 4, 5 or 6;
    $R^{10}$ and $R^{11}$ independently represent a hydrogen atom, a $C_1$-$C_6$ alkyl group, a benzyl;
  $R^5$ and $R^6$ independently represent a hydrogen atom, a $C_1$-$C_6$ alkyl group, a halogen, —OH, a $C_1$-$C_6$ alkoxy group, —NH$_2$, —NO$_2$, a group of formula -$(L^3)_v$-[P(O)(OR$^{21}$)$_2$]$_w$ wherein:
    $L^3$, identical or different, represents a —CHR$^{22}$ group, O;
    v represents 0 or 1;
    w represents 1 or 2;
    $R^{21}$ and $R^{22}$ independently represent a hydrogen atom, a methyl, an ethyl, a benzyl;
  $R^1$ represents a hydrogen atom, a $C_1$-$C_6$ alkyl group;
  $R^2$ represents a hydrogen atom, $C_1$-$C_6$ alkyl group, —OH.

According to the invention, the compound may be a compound of formula (B4a) wherein:

Q represents a hydrogen atom, —CN, —NR$^1$R$^2$, a C$_1$-C$_2$ alkyl-amine group;

T$^4$ represents:
- a hydrogen atom;
- a branched or non-branched, substituted or non-substituted C$_1$-C$_{12}$ alkyl group;
- a group of formula (L)$_m$-P(O)(OT$^1$)$_2$ wherein:
  - L represents O;
  - m represents 1;
  - T$^1$ independently represents a hydrogen atom, a methyl, an ethyl, a benzyl;
- a cyclohexyl group;

G$^1$ represents a hydrogen atom, a C$_1$-C$_6$ alkyl group, —OH, a group of formula -(L$^1$)$_q$-P(O)(OR$^7$)$_2$ wherein:
  - L$^1$, identical or different, represents O, CHR$^8$:
  - q represents 0, 1, 2, 3, 4, 5 or 6;
  - R$^7$ and R$^8$ independently represent a hydrogen atom, a methyl, an ethyl, a benzyl;

R$^5$ and R$^6$ independently represent a hydrogen atom, a C$_1$-C$_6$ alkyl group, a halogen, —OH, a C$_1$-C$_6$ alkoxy group, —NH$_2$, —NO$_2$, a group of formula -(L$^3$)$_v$-[P(O)(OR$^{21}$)$_2$]$_w$ wherein:
  - L$^3$, identical or different, represents a —CHR$^{22}$ group, O;
  - v represents 0 or 1;
  - w represents 1 or 2;
  - R$^{21}$ and R$^{22}$ independently represent a hydrogen atom, a methyl, an ethyl, a benzyl;

R$^1$ represents a hydrogen atom, a C$_1$-C$_6$ alkyl group;

R$^2$ represents a hydrogen atom, a C$_1$-C$_6$ alkyl group, —OH.

According to the invention, the compound may be a compound of formula (B5a) wherein:

Q represents a hydrogen atom, —CN, —NR$^1$R$^2$, a C$_1$-C$_2$ alkyl-amine group;

T$^5$ represents a residue of an amino acid linked by its N-terminal position and selected from the group consisting of cysteine, glycine, lysine, phenylalanine and serine;

R$^5$ and R$^6$ independently represent a hydrogen atom, a C$_1$-C$_6$ alkyl group, a halogen, —OH, a C$_1$-C$_6$ alkoxy group, —NH$_2$, —NO$_2$, a group of formula -(L$^3$)$_v$-[P(O)(OR$^{21}$)$_2$]$_w$ wherein:
  - L$^3$, identical or different, represents a —CHR$^{22}$ group, O;
  - v represents 0 or 1;
  - w represents 1 or 2;
  - R$^{21}$ and R$^{22}$ independently represent a hydrogen atom, a methyl, an ethyl, a benzyl;

R$^1$ represents a hydrogen atom, a C$_1$-C$_6$ alkyl group;

R$^2$ represents a hydrogen atom, a C$_1$-C$_6$ alkyl group, —OH.

The different objects of the invention and their embodiments will be better understood upon reading the examples which follow. These examples are given as an indication, without any limitation.

EXAMPLE 1

(E)-2-cyano-3-(3,4-dihydroxyphenyl) 3-phenylprop-2-ynyl acrylate

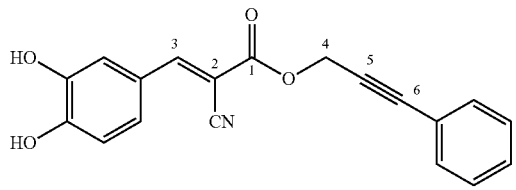

C$_{19}$H$_{13}$NO$_4$
M = 319.08 g · mol$^{-1}$

Under argon, iodobenzene (8.9 mmol) was solubilized in a mixture of 1,2-dimehoxythane (10 mL) and water (10 mL). Next, were successively added potassium carbonate (21.7 mmol), copper iodide (0.36 mmol), triphenylphosphine (0.72 mmol) and 10% palladium on carbon (0.02 mmol Pd) and then left with stirring for 20 mins at room temperature. Propargylic alcohol was then added and the reaction mixture was brought to 80° C. for 18 h. After cooling, the reaction mixture was filtered on Celite® and the filter evaporated in vacuum. Next, the residue was dissolved in 20 mL of ethyl acetate and 20 mL of water and the aqueous phase was extracted with ethyl acetate (3×20 mL), dried with magnesium sulfate, filtered and evaporated in vacuum. The crude product is purified on silica (10% cyclohexane ethyl acetate) and the alcohol is isolated (99%) in the form of a colorless oil. $^1$H NMR (400 MHz, CDCl$_3$): δ 7.59-7.24 (m, 5H), 4.52 (s, 2H), 2.12 (se, 1H).

Under argon, cyanoacetic acid (1.0 mmol) and the alcohol (0.8 mmol) were solubilized in 4 mL anhydrous dichloromethane and N,N'-dicyclohexylcarbodiimide (1.0 mmol) and N,N-dimethylaminopyridine (cat.) were successfully added at 0° C. After total consumption of the acid (CLC), the formed white precipitate was filtered and the filtrate evaporated in vacuum. The residue was purified on silica, (SiO$_2$, 20% ethyl acetatecyclohexane) and the ester was obtained as a colorless oil (52%). $^1$H NMR (400 MHz, CDCl$_3$): δ 7.64-7.28 (m, 5H), 5.06 (s, 2H), 3.57 (s, 2H).

Under argon, 3,4-dihydroxybenzaldehyde (0.45 mmol) and piperidine (cat.) were added on the 3-phenylprop-2-ynyl 2-cyanoacetate (0.45 mmol) solubilized in 4 mL of anhydrous dichloromethane. Next, at room temperature the reaction mixture was stirred until total consumption of the 3-phenylprop-2-ynyl 2-cyanoacetate (TLC). After adding an aqueous solution saturated with magnesium chloride, the organic phase was extracted with ethyl acetate (3×8 mL), dried with magnesium sulfate and filtered. After evaporation in vacuum of the solvent, the residue was purified on silica (SiO$_2$, 30% ethyl acetatecyclohexane) and the (E-2-cyano-3-(3,4-dihydroxyphenyl) 3-phenylprop-2-ynyl acrylate ester was obtained in the form of a pale yellow solid (40%). $^1$H NMR (400 MHz, MeOD-d$_4$): δ 8.17 (s, 1H), 7.69-7.27 (m, 8H), 5.14 (s, 2H). HR-ESI-MS calculated for C$_{19}$H$_{13}$NO$_4$ (M+Na$^+$)=342.0732; found 342.0742.

EXAMPLE 2

(E)-2-cyano-3-(furan-3-yl) acrylic acid

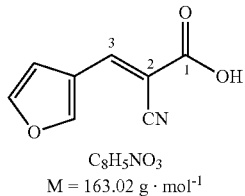 [SMILES: N#C/C(=C\c1ccoc1)C(=O)O]

C$_8$H$_5$NO$_3$
M = 163.02 g·mol$^{-1}$

Under argon, the cyanoacetic acid (7.05 mmol) was dissolved in anhydrous dichloromethane (10 mL); t-butanol (7.76 mmol), N,N'-dicyclohexylcarbodiimide (7.05 mmol) were added at room temperature. After one hour, the precipitate was filtered in vacuum and the filtrate evaporated in vacuum. The residue was purified on silica (SiO$_2$, 10% ethyl acetatecyclohexane) and a t-butyl ester was obtained in the form of a colorless oil (61%). $^1$H NMR (400 MHz, CDCl$_3$): δ: 3.39 (s, 2H), 1.51 (s, 9H).

Under argon, the 3-furaldehyde (2.34 mmol) and the piperidine (cat.) were added on the butyl ester (2.12 mmol) solubilized in 15 mL of anhydrous dichloromethane. Mixed at room temperature, the reaction mixture was stirred until total consumption of the ester (TLC). After adding an aqueous solution saturated with ammonium chloride, the aqueous phase was extracted with ethyl acetate (3×8 mL), dried with magnesium sulfate and filtered. After evaporation in vacuum of the solvent, the residue was purified on silica (eluent: cyclohexane and ethyl acetate) and the alkene was obtained as a yellow powder (45%). $^1$H NMR (400 MHz, CDCl$_3$): δ 8.03 (s, 1H), 8.02-7.23 (m, 3H), 1.56 (se, 9H).

Under argon, the alkene (0.29 mmol) was solubilized in (1 mL). After 1 h 30 mins of stirring at room temperature, the trifluoroacetic acid was evaporated in vacuum. The residue was triturated with ether and the ether was then evaporated in vacuum. The experiment was repeated 3 times and (E)-2-cyano-3-(furan-3-yl) acrylic acid as a pale yellow powder (90%) was obtained. $^1$H NMR (400 MHz, MeOD-d$_4$): δ 8.28 (s, 1H), 8.26 (s $^1$H, 1H), 7.73 (m, 1H), 7.27 (d, J=1.9 Hz, 1H). HR-ESI-MS calculated for C$_8$H$_5$NO$_3$ (M+Na$^+$)=186.0167; found 186.0170.

EXAMPLE 3

6.7-dihydroxy-1H-indole-2-carboxylic acid

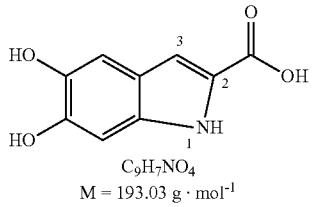 [SMILES: O=C(O)c1cc2cc(O)c(O)cc2[nH]1]

C$_9$H$_7$NO$_4$
M = 193.03 g·mol$^{-1}$

DL-DOPA (5 mmol) was solubilized in water (500 mL). After 5 mins of stirring at room temperature, a solution of potassium ferricyanide (20 mmol) in 60 mL of water was added. Next, a 1 M soda aqueous solution was added until pH=13. After 20 mins of stirring under argon, the reaction mixture was acidified with a 6 M hydrochloric acid aqueous solution until pH=2 and the aqueous phase was extracted with ethyl acetate (3×100 mL). The collected organic phases were dried and filtered in vacuum and a pale brown solid was obtained and washed with a saline solution containing 1 mmol of Na$_2$S$_2$O$_5$ and then with a saline solution (2×100 mL). The organic phase was dried with magnesium sulfate, filtered and evaporated in vacuum. The residue was purified on silica (SiO$_2$, 90% ethyl acetate methanol) and 6,7-dihydroxy-1H-indole-2-carboxylic acid was obtained as a pale brown powder. $^1$H NMR (400 MHz, MeOD-d$_4$): δ 6.95 (s, 1H); 6.93 (s, 1H); 6.82 (s, 1H).

EXAMPLE 4

(E)-2-carboxy-3-(3,4-dihydroxyphenyl)prop-2-en-1-ammonium chloride

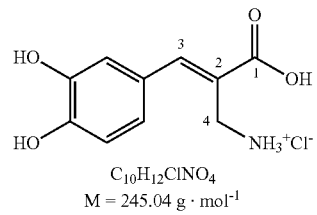

C$_{10}$H$_{12}$ClNO$_4$
M = 245.04 g·mol$^{-1}$

Triethylphosphonoacetate (44.62 mmol) was added to a methanol solution (108 mL) containing paraformaldehyde (89.24 mmol) and piperidine (4.46 mmol). After 24 hours of refluxing, the solvent was evaporated in vacuum and the primary alcohol was obtained. The residue was solubilized in toluene (60 ml), treated with para-toluenesulfonic acid monohydrate (4.46 mmol) and the reaction mixture was refluxed in a Dean-Stark setup. After 16 h, the mixture was concentrated in vacuum and distilled under reduced pressure in order to obtain vinyl phosphonate as a pale yellow oil (92%). $^1$H NMR (400 MHz, CDCl$_3$): δ 6.82 (dd, J=2 Hz and J$_{H-P}$=41.9 Hz, 1H), 6.62 (dd, J=2 Hz and J$_{H-P}$=20.9 Hz, 1H), 4.18 (m, 6H), 1.36 (m, 3H), 1.33 (m, 6H).

A solution of t-butoxycarbonylamine (5.08 mmol) in anhydrous tetrahydrofurane (7 ml) was added, with stirring, dropwise, to a suspension of sodium hydride (50% in the oil, 9.30 mmol) in anhydrous tetrahydrofurane (15 mL) under argon at 0° C. The reaction mixture was stirred for 30 mins at 0° C. and a solution of ethyl 2-diethoxyphosphoryl acrylate (4.23 mmol) in anhydrous tetrahydrofurane (7 mL) was added. The reaction was stirred for 1 h at room temperature. Water (20 mL) was then added to the reaction mixture. The latter was acidified to pH 5 with a 1 M hydrochloric acid aqueous solution. The aqueous phase was extracted with ethyl acetate (3×30 mL), dried with magnesium sulfate and evaporated in vacuum. Finally, the residue was purified by column chromatography (70% ethyl acetate/cyclohexane) in order to obtain the ethyl 3-t-butoxycarbonylamino-2-diethoxyphosphoryl-3-propionate as a colorless oil (62%). $^1$H NMR (400 MHz, CDCl$_3$): δ 5.10 (se, 1H), 4.15 (m 6H), 3.60 (m, 2H), 3.26 (td, J=23.0, 7.0 Hz, 1H), 1.40 (se, 9H), 1.33 (m, 6H), 1.25 (t, J=7.0 Hz, 3H).

Under argon, a solution of ethyl 3-t-butoxycarbonylamino-2-diethoxyphosphoryl-3-propionate (6.56 mmol) in anhydrous tetrahydrofurane (11 mL) was added dropwise on sodium hydride (50% in a mineral oil, 9.2 mmol) suspended in anhydrous tetrahydrofurane (11 mL) at 0° C.

The reaction mixture was stirred for 30 mins at 0° C. and then 3,4-bis(methoxymethoxy)benzaldehyde (5.05 mmol) was solubilized in anhydrous tetrahydrofurane (11 mL) which is added dropwise. After full consumption of the aldehyde (TLC), the reaction was stopped with water. The aqueous phase was extracted with ethyl acetate (3×20 mL), dried with magnesium sulfate and filtered. After evaporation in vacuum of the solvent, the residue was purified on silica by column chromatography (20% ethyl acetate cyclohexane) and the alkene (E) was obtained as a colorless oil (60%). $^1$H NMR (400 MHz, CDCl$_3$): δ 7.69 (s, 1H), 7.15-7.33 (m, 3H), 5.25 and 5.28 (2×s, 4H), 5.8 (se, 1H), 4.26 (q, J=7.0 Hz, 2H), 4.20 (d, J=7.0 Hz, 2H), 3.50 (s, 6H), 1.42 (se, 9H), 1.30 (t, J=7.0 Hz).

The alkene E (0.642 mmol) was solubilized in methanol (2.5 mL) and then a 1M aqueous solution of lithium hydroxide (1.92 mmol) was added. After full consumption of the ester (TLC), the solvent was evaporated in vacuum. The aqueous phase was treated with a 1 M hydrochloric acid aqueous solution down to pH =2. Next, the aqueous phase was extracted with ethyl acetate (3×10 mL), dried with magnesium sulfate and filtered. After evaporation of the solvent in vacuum, the desired acid (91%) is obtained. $^1$H NMR (400 MHz, CDCl$_3$): δ 7.69 (s, 1H), 7.15-7.33 (m, 3H), 5.25 and 5.28 (2×s, 4H), 5.8 (se, 1H), 4.20 (d, J=7.0 Hz, 2H), 3.50 (s, 6H), 1.42 (se, 9H).

To a solution of (E)-3-(3,4-bis(methoxymethoxy)phenyl)-2-((t-butoxy-carbonyl-amino)-methyl) acrylic acid (0.25 mmol) in methanol (50 mL) was added a 10% hydrochloric acid aqueous solution (10 mL). The reaction mixture was stirred for 2 days at room temperature. Next, the solvent was evaporated in vacuum and the residue was dissolved in 2 mL of dichloromethane and then methanol was added, causing precipitation of the compound. The precipitate was filtered under reduced pressure and (E)-2-carboxy-3-(3,4-dihydroxyphenyl)prop-2-en-1-ammonium chloride was obtained as a white powder (40%). $^1$H NMR (400 MHz, DMSO-d$_6$): δ 13.00 (s, 1H), 9.71 (se, 1H), 9.28 (se, 1H), 8.13 (se, 3H), 7.73 (s, 1H), 6.99 (d, J=1.7 Hz, 1H), 6.87 (d, J=1.7 Hz, 1H), 6.86 (dd, J=8.0, 1.7 Hz, 1H), 3.84 (se, 2H). HR-ESI-MS calculated for C$_{10}$H$_{12}$NO$_4$(M+H$^+$)=210.0766; found 210.0776.

EXAMPLE 5

(Z)-2-fluoro-3-phenylacrylic acid

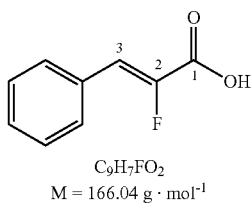 [SMILES: O=C(O)/C(F)=C/c1ccccc1]

C$_9$H$_7$FO$_2$
M = 166.04 g · mol$^{-1}$

To a freshly distilled solution of diisopropylamine (19.3 mmol) in anhydrous tetrahydrofurane (8 mL) was added 1.6 M n-butyl lithium (18.8 mmol) at −30° C. The solution was stirred for 30 mins at −30° C. It was then transferred into a solution consisting of ethyl 2-fluoroacetate (4.7 mmol) and of trimethylsilyl chloride (28.3 mmol) in 45 mL of anhydrous tetrahydrofurane, at −78° C. The reaction mixture was stirred and then left to return to 0° C. over a period of 4 h. The reaction mixture was treated with a saturated sodium carbonate solution (100 mL) at 0° C. The aqueous phase was extracted with ether (3×50 mL). The organic phase was dried on magnesium sulfate, filtered and then concentrated (20 mL). It was washed with a tartaric solution (50 mL) and stirred for 12 h at room temperature. The aqueous phase was extracted twice with ether (2×20 mL). The organic phases are collected and dried with magnesium sulfate and concentrated under reduced pressure. The residue was purified by chromatography (SiO$_2$, 10% diethyl ether/pentane) in order to lead to ethyl 2-fluoro-2-(trimethylsilyl)acetate as a colorless oil (800 mg, 95%). EI-MS (70 eV) mz: 178. $^1$H NMR (400 MHz, CDCl$_3$): δ 4.95 (d, J=48.1 Hz, 1H), 4.20 (q, J=7.0 Hz, 2H), 1.28 (t, J=7.0 Hz, 3H), 0.18 (s, 9H).

To a freshly distilled solution of diisopropylamine (2.57 mmol) in anhydrous tetrahydrofurane (13 mL) was added a 1.6 M solution de n-BuLi (2.57 mmol) à −30° C.). La solution was stirred for 30 mins at −30° C. and then cooled to −78 ° C. Ethyl 2-fluoro-2-(trimethylsilyl)acetate (2.25 mmol), dissolved in anhydrous tetrahydrofurane (2 mL) was added to the formed LDA solution and the stirred for 40 mins at −78 ° C. followed by the addition of a solution of benzaldehyde (2.31 mmol) in anhydrous tetrahydrofurane (2 mL). The solution was brought to −78 ° C. until total disappearance of ethyl 2-fluoro-2-(trimethylsilyl)acetate (tracked by GC-MS). The reaction mixture was treated with a saturated solution of ammonium chloride (30 mL) at 0° C. The aqueous phase was extracted with ethyl acetate (3×20 mL). The collected organic phases are dried with magnesium sulfate and then concentrated under reduced pressure. The residue was purified by silica gel chromatography (5% ethyl acetatecyclohexane) so as to lead to ethyl (Z)2-fluoro-3-phenylacrylate as a colorless oil (216.7 mg, 50%). EI-MS (70 eV): mz=194. $^1$H NMR (400 MHz, CDCl$_3$): δ 7.65-7.31 (m 5H), 6.92 (d, J=35.2 Hz, 1H), 4.36 (q, J=7 Hz, 2H), 1.40 (t, J=7 Hz, 3H).

The ester (1.12 mmol) was solubilized in methanol and a 1.5 M soda aqueous solution (2.23 mmol) is then added. After a full consumption of the ester (TLC), the solvent was evaporated in vacuum. The aqueous phase was treated with a 1M hydrochloric acid solution down to pH=2. Next, the aqueous phase was extracted with ethyl acetate (3×10 mL), tried with magnesium sulfate and filtered. After evaporation of the solvent in vacuum, the (Z)-2-fluoro-3-phenylacrylic acid was obtained as a white solid (91%). $^1$H NMR (400 MHz, CDCl$_3$): δ 8.75 (se, 1H), 7.67-7.38 (m, 5H), 7.07 (d, J=34.6 Hz, 1H). HR-ESI-MS calculated for C$_9$H$_6$O$_2$F (M−H$^+$)=165.0352; found 165.0341

EXAMPLE 6

(E)-2-cyano-3-(1H-indol-2-yl)acrylic acid

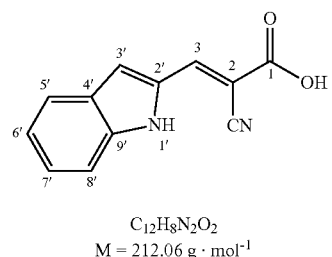

C$_{12}$H$_8$N$_2$O$_2$
M = 212.06 g · mol$^{-1}$

Sulfuric acid (248 µL) was added to a solution of indole-2-carboxylic acid (2.48 mmol) in absolute ethanol (8 mL).

The reaction mixture was refluxed for 15 h, and sulfuric acid (248 μL) was added. The reaction mixture was heated for a further 3 h. After cooling to room temperature, the solvent was evaporated under reduced pressure, the residue was dissolved in 10 mL of DCM, and the resulting solution was washed with a saturated sodium carbonate aqueous solution (3×20 mL), water (10 mL) and brine (10 mL). The organic phase is dried with magnesium sulfate, filtered, evaporated under reduced pressure in order to obtain a white powder (365.8 mg, 77%). $^1$H NMR (400 MHz, CDCl$_3$): δ 8.93 (s, 1H), 7.70 and 7.43 (2×d, J=8.1 Hz, 2H), 7.36-7.24 (m, 2H), 7.16 (t, J=7.3 Hz, 1H), 4.42 (q, J=7.1 Hz, 2H), 1.42 (t, J=7.1 Hz, 3H). A solution of ethyl 1H-indole-2-carboxylate (2.65 mmol) in anhydrous tetrahydrofurane (10 mL) was added dropwise to a cooled solution (0° C.), a lithium aluminium hydride (3.98 mmol) suspension in anhydrous tetrahydrofurane (10 mL) and the mixture was stirred for 2 h. The reaction was stopped by dropwise addition of (5 mL) and washed with water (20 mL). The organic phase was dried with magnesium sulfate and concentrated under reduced pressure. The residue was purified by column chromatography (SiO$_2$, 40% ethyl acetate cyclohexane) in order to obtain a white powder (386.7 mg, 99%). $^1$H NMR (400 MHz, CDCl$_3$): δ 8.38 (se, 1H), 7.61 and 7.37 (2×d, J=8.0 Hz, 2H), 7.21 and 7.13 (m, 2H), 6.43 (t, J=7.3 Hz, 1H), 4.84 (se, 2H), 1.93 (se, 1H).

(1H-indol-2-yl) methanol (2.63 mmol) was dissolved in anhydrous tetrahydrofurane (40 mL) and treated with manganese oxide (30.24 mmol). After stirring for 18 h at room temperature, the reaction mixture was filtered and the filtrate concentrated under reduced pressure in order to obtain a brown powder (302 mg, 79%). $^1$H NMR (400 MHz, CDCl$_3$): δ 9.86 (s, 1H), 9.30 (se, 1H), 7.76 and 7.48 (2×d, J=8.1 Hz, 2H), 7.40-7.19 (m, 2H), 7.29 (s, 1H).

Under argon, cyanoacetic acid (7.05 mmol) was dissolved in anhydrous dichloromethane (10 mL); t-butanol (7.76 mmol) and N,N'-dicyclohexylcarbodiimide (7.05 mmol) are added at room temperature. After 1 h, the precipitate formed was filered and the filtrate evaporated in vacuum. The residue was purified on silica (SiO$_2$, 10% ethyl acetate cyclohexane) and the t-butyl ester is obtained as a colorless oil (61%). $^1$H NMR (400 MHz, CDCl$_3$): δ: 3.39 (s, 2H), 1.51 (s, 9H).

Under argon, indole-2-carbaldehyde (1.91 mmol) and piperidine (cat.) are added on t-butyl 2-cyanoacetate (1.91 mmol) solubilized in 4 mL of anhydrous dichloromethane. Next, at room temperature, the reaction mixture was stirred until t-butyl 2-cyanoacetate was fully consumed (TLC). After adding a saturated ammonium chloride solution, the aqueous phase was extracted with ethyl acetate (3×8 mL), dried with magnesium sulfate and filtered. After evaporation in vacuum of the solvent, the residue was purified on silica (SiO$_2$, 30% ethyl acetate/cyclohexane) and the ester is obtained as a yellow solid (69%). $^1$H NMR (400 MHz, CDCl$_3$): δ 9.50 (se, 1H), 8.09 (s, 1H), 7.67 and 7.46 (2×d, J=8.1 Hz, 2H), 7.42-7.17 (m, 3H,), 1.59 (se, 9H).

Under argon, the t-butyl ester (0.74 mmol) was solubilized in trifluoroacetic acid (3 mL). After 1 h 30 mins of stirring at room temperature, trifluoroacetic acid was evaporated in vacuum. The residue was triturated with ether followed by evaporation of the latter. The experiment was repeated 3 times and (E)-2-cyano-3-(1 H-indol-2-yl)acrylic acid was obtained as a pale yellow solid (78%). $^1$H NMR (400 MHz, MeOD-d$_4$): δ 11.17 (se, 1H), 8.27 (s, 1H), 7.68 and 7.46 (2×d, J=8.2 Hz, 2H), 7.65 (s, 1H), 7.32 and 7.12 (2×t, J=7.5 Hz, 2H). HR-ESI-MS calculated for C$_{12}$H$_8$N$_2$O$_2$ (M−H$^+$)=211.0508; found 211.0514.

EXAMPLE 7

(E)-tert-butyl 3-(4-(bis(benzyloxy)phosphoryloxy) phenyl)-2-cyanoacrylate

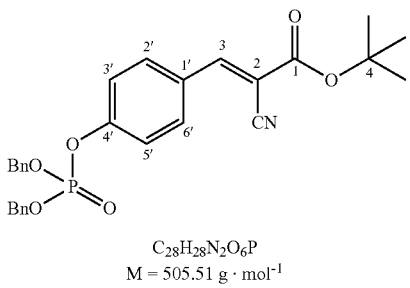 [SMILES: CC(C)(C)OC(=O)/C(C#N)=C/c1ccc(OP(=O)(OCc2ccccc2)OCc2ccccc2)cc1]

C$_{28}$H$_{28}$N$_2$O$_6$P
M = 505.51 g · mol$^{-1}$

Under argon, N-chlorosuccinimide (1.05 mmol) was dissolved in anhydrous toluene (5 mL), and then benzyl phosphite (0.95 mmol) was added. The reaction mixture was stirred for 2 hours at room temperature, and then filtered in order to remove the precipitate. The thereby obtained filtrate was concentrated under reduced pressure in order to obtain dibenzylphosphorochloridate as a colorless oil (95%).

$^1$H NMR (400 MHz, CDCl$_3$): δ 7.35 (bs, 10H), 5.25 (m, 4H).

Under argon, cyanoacetic acid (7.16 mmol) and t-butanol (6.51 mmol) are dissolved in anhydrous dichloromethane (30 mL) and cooled to 0° C. DCC (7.16 mmol) and DMAP (cat.) are added to the solution. The medium is stirred for 4 hours at 0° C. and 1 h at room temperature. The reaction mixture is filtered, then concentrated under reduced pressure. The thereby obtained is purified by column chromatography (SiO$_2$, 20% EtOAccyclohexane) in order to obtain the t-butyl ester as a colorless oil (86%).

$^1$H NMR (400 MHz, CDCl$_3$): δ 4.23 (q, J=6.5 Hz, 2H, H-3), 3.44 (s, 2H, H-2), 1.28 (t, J=6.5 Hz, 3H, H-4).

Under argon, 4-hydroxybenzaldehyde (0.53 mmol) and piperidine (cat.) were added to the t-butyl ester (0.53 mmol) solubilized in anhydrous dichloromethane. Next, the reaction mixture was stirred, at room temperature, until the ester is totally consumed (TLC). After adding a saturated ammonium chloride aqueous solution, the organic phase was extracted with ethyl acetate (3×8 mL), dried with magnesium sulfate and filtered. After evaporation in vacuum of the solvent, the residue was purified on silica (eluent: cyclohexane and ethyl acetate) in order to obtain the compound (E)-tert-butyl 2-cyano-3-(4-hydroxyphenyl)acrylate as a brown powder (71%).

$^1$H NMR (400 MHz, MeOD-d$_4$): δ 8.13 (s, 1H, H-3), 7.96 (m, 2H, H-2' and H-6'), 6.93 (m, 2H, H-3' and H-5'), 1.58 (s, 9H, 3×CH$_3$).

Under argon, to a solution of (E)-tert-butyl 2-cyano-3-(4-hydroxyphenyk)acrylate (0.41 mmol) in acetonitrile (2 mL), were successively added at room temperature, dibenzyl chlorophosphonate (0.61 mmol) and then potassium carbonate (1.64 mmol). The reaction mixture was stirred for 5 days, and then treated by adding an aqueous solution. The aqueous phase was extracted with ethyl acetate (3×8 mL), dried with magnesium sulfate and filtered. After evaporation in vacuum of the solvent, the residue was purified on silica (SiO$_2$, EtOAccyclohexane) and the compound is obtained as a colorless oil (20%). $^1$H NMR (400 MHz, CDCl$_3$): δ 8.09 (s, 1H), 7.90 (d, J=8.8 Hz, 2H), 7.38-7.29 (m, 10H), 7.21 (d, J=8.3 Hz, 2H,), 5.13 (d, $J_{P,H}$=10.5 Hz, 4H), 1.59 (s, 9H).

EXAMPLE 8

Evaluation of the Activation of TREK-1 Channels bt the Compounds According to the Invention Xenope ovocytes without their follicle cells are injected with 50 ng of cRNA coding for the TREK-1 channel.

18-24 h after injection, the TREK-1 currents are recorded with the double electrode technique. In a perfusion chamber of 0.3 mL, the ovocyte is impaled with two standard microelectrodes (resistance 1-2.5 M) filled with a 3M KCl solution and maintained at an imposed voltage by means of a Dagan TEV 200 amplifier in a ND96 standard solution (96 mM NaCl, 2 mM KCl, 1.8 mM $CaCl_2$, 2 mM $MgCl_2$, 5 mM HEPES, pH 7.4 with NaOH) for 3 mins. And then a solution of the compound (20 nM) is perfused for 15 minutes, followed by rinsing with ND96 for 6 minutes. Stimulation of the preparation, data acquisition and analyses are carried out by using the software package pClamp.

The results are shown in Table 1.

TABLE 1

| Compound | R (in vitro) |
|---|---|
| 3,4-dihydroxyphenyl acrylic acid with CH2NH3+Cl- substituent | 2.87 |
| 5,6-dihydroxyindole-2-carboxylic acid | 1.31 |
| 3,4-dihydroxyphenyl α-cyano acrylate, 3-phenylprop-2-yn-1-yl ester | 2.2 |
| 3-furyl α-cyano acrylic acid | 1.43 |
| indol-2-yl α-cyano acrylic acid | 2.44 |
| phenyl α-fluoro acrylic acid | 1.44 |

TABLE 1-continued

| Compound | R (in vitro) |
|---|---|
| 3,4-dihydroxyphenyl α-cyano acrylate, undecyl ester | 1.12 |
| 3,4-dihydroxyphenyl α-cyano acrylate, cyclohexyl ester | 1.14 |
| 3,4-dihydroxyphenyl α-cyano acrylate, tert-butyl ester | 1.20 |
| 3,4-dihydroxyphenyl α-cyano acrylate, isopentyl ester | 1.22 |

The results show that the compounds according to the invention have the property of activating the TREK-1 channels.

EXAMPLE 9

Evaluation of the Analgesic Effect of the Compounds According to the Invention

The animals (mice weighing 15-20 g) are pretreated with the compound (10 mg/kg) or the carrier (control) 15 mins before injecting acetic acid (0.6% solution, 10 mL/kg) into the peritoneal cavity of the animal where it activates the nociceptors directly and/or causes an inflammation of the viscera (subdiaphragmatic organs) and subcutaneous (muscle wall) inflammation of the tissues. The number of induced abdominal cramps, determined for 15 mins after injection of acetic acid is used as a pain parameter. Pain inhibition (an analgesic effect) is determined by comparing the number of induced cramps in the presence and in the absence of the molecules.

The results are shown in Table 2.

TABLE 2

| Compound | Inhibition of pain in % (in vivo) |
|---|---|
| 3,4-dihydroxyphenyl acrylic acid with CH2NH3+Cl- substituent | 50 |

TABLE 2-continued

| Compound | Inhibition of pain in % (in vivo) |
|---|---|
| 5,6-dihydroxy-1H-indole-2-carboxylic acid | 51 |
| 3,4-dihydroxyphenyl cyanoacrylate 3-phenylprop-2-yn-1-yl ester | 22 |
| 3-(furan-3-yl)-2-cyanoacrylic acid | 31 |
| 2-cyano-3-(1H-indol-2-yl)acrylic acid | 26 |
| 2-fluoro-3-phenylacrylic acid | 34 |
| 3,4-dihydroxyphenyl cyanoacrylate undecyl ester | 45 |
| 3,4-dihydroxyphenyl cyanoacrylate cyclohexyl ester | 55 |
| 3,4-dihydroxyphenyl cyanoacrylate tert-butyl ester | 43 |
| 3,4-dihydroxyphenyl cyanoacrylate isopentyl ester | 27 |

The results show that the compounds according to the invention have significant pain inhibition properties.

What is claimed is:

1. A compound of formula (A1):

$$\text{(A1)}$$

wherein:
R represents:

Q represents —CN;
X represents O, or —NH;
T represents:
a hydrogen atom;
a phenyl group;
a group

;

a cyclohexyl group;
$Q^2$ represents O, or NH;
or a pharmaceutically acceptable salt of said compound.

2. The compound according to claim 1, wherein:
Q represents —CN;
$Q^2$ represents O, or NH
X represents O or NH
T represents:
a hydrogen atom;
a phenyl group;
a group

.

3. The compound according to claim 1, wherein:
$Q^2$ represents O;
X represents O;
T represents H.

4. The compound according to claim 1 of formula (1b):

$$\text{(1b)}$$

wherein $Q^2$, Q, X and T are as defined in claim 1.

5. A method for treatment of pain comprising administering to a patient, a composition comprising a compound according to claim 1.

6. A method for treatment of pain comprising administering to a patient, a composition comprising a compound according to claim 2.

7. A method for treatment of pain comprising administering to a patient, a composition comprising a compound according to claim 1.

8. A method for treatment of pain comprising administering to a patient, a composition comprising a compound according to claim 3.

* * * * *